United States Patent [19]
Morrow

[11] Patent Number: 4,982,166
[45] Date of Patent: Jan. 1, 1991

[54] METHOD AND APPARATUS FOR COMBINING TWO LOWER POWER LASER BEAMS TO PRODUCE A COMBINED HIGHER POWER BEAM

[76] Inventor: Clifford E. Morrow, 576 Hatchery Rd., North Kingstown, R.I. 02852

[21] Appl. No.: 317,678

[22] Filed: Mar. 1, 1989

[51] Int. Cl.$^5$ .............................................. H01S 3/00
[52] U.S. Cl. ..................................... 330/4.3; 350/370; 350/401
[58] Field of Search ..................... 330/4.3; 332/7.51; 350/370, 389, 401, 174; 372/97, 106

[56] References Cited

U.S. PATENT DOCUMENTS

| | | | |
|---|---|---|---|
| 3,671,747 | 6/1972 | Duguay | 332/7.51 |
| 4,019,151 | 4/1977 | Brueckner et al. | 350/401 |
| 4,105,337 | 8/1978 | Bjorklund et al. | 350/370 |
| 4,371,784 | 2/1983 | Rodgers | 250/231 GY |
| 4,389,617 | 6/1983 | Kurnit | 330/4.3 |
| 4,720,162 | 1/1988 | Mochizuki et al. | 350/370 |
| 4,926,366 | 5/1990 | Cuykendall et al. | 364/713 |

FOREIGN PATENT DOCUMENTS

| | | | |
|---|---|---|---|
| 1174882 | 9/1984 | Canada | 350/401 |
| 140508 | 5/1985 | European Pat. Off. | 350/401 |

Primary Examiner—Nelson Moskowitz
Attorney, Agent, or Firm—Kenyon & Kenyon

[57] ABSTRACT

Apparatus for combining two laser beams each having a power level into a common colinear laser beam having a power level that is the sum of the power levels of the two laser beams comprising a support, a polarization selective device disposed on the support having a first surfaces upon which a first of the laser beams impinges for transmitting the first laser beam with substantially full power transmission along an axis and having a second surface upon which the second laser beam impinges for reflecting the second laser beam with substantially full power along the axis, resulting in a common colinear beam along the axis, and suitable optical and/or mechanical devices disposed on the support for providing the first and second laser beams to the polarization selective device, the first and second laser beams being substantially orthogonally polarized with respect to each other.

26 Claims, 1 Drawing Sheet

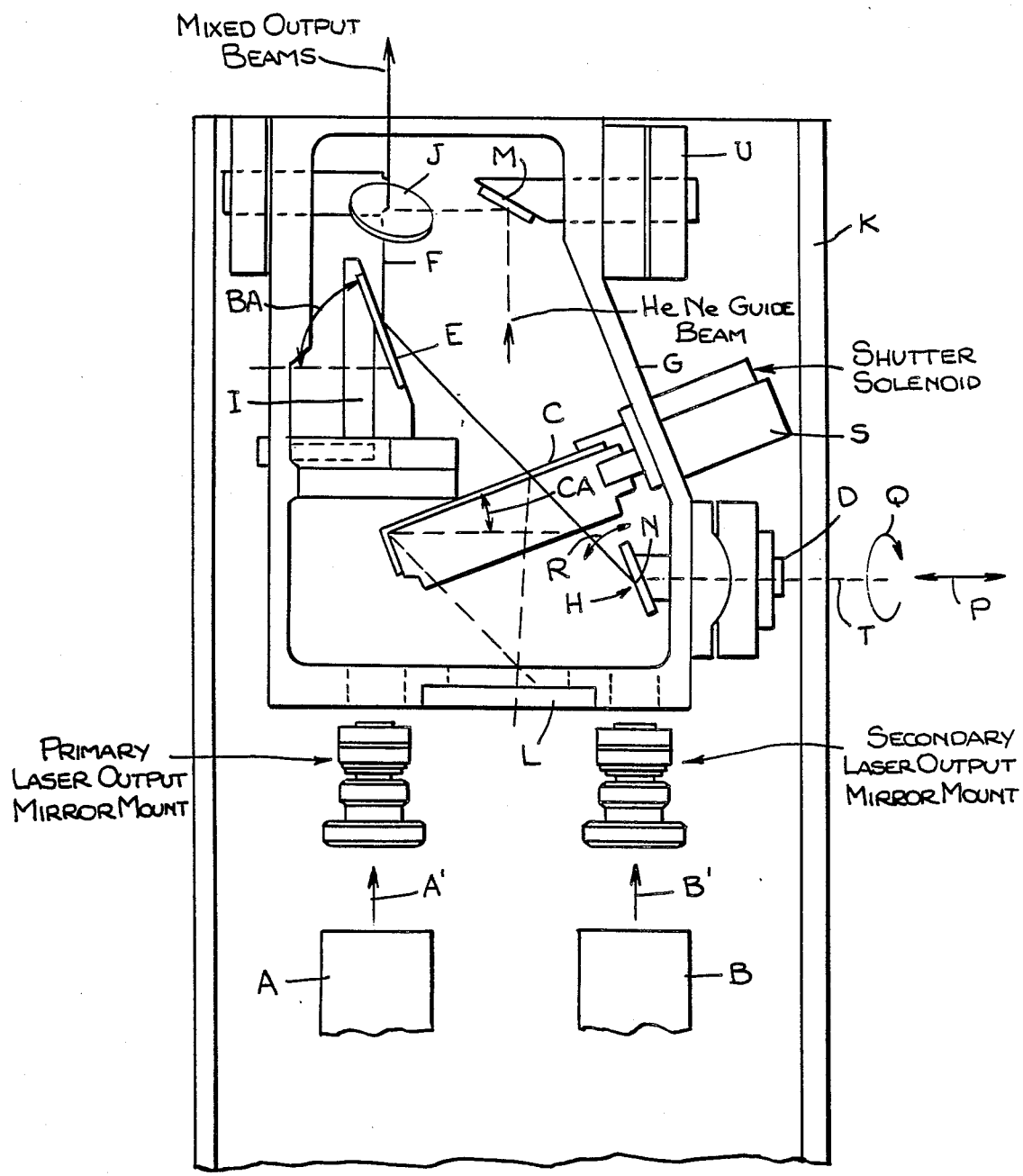

METHOD AND APPARATUS FOR COMBINING TWO LOWER POWER LASER BEAMS TO PRODUCE A COMBINED HIGHER POWER BEAM

BACKGROUND OF THE INVENTION

The present invention relates to laser beam technology, and in particular, to an apparatus for combining the laser beams from two separate lasers to provide an output laser beam having a power which is approximately the sum of each of the individual laser beams. In particular, the invention avoids the difficulties encountered in a folded cavity laser, and especially misalignment problems which occur during movement of such folded cavity lasers, i.e., in surgical laser systems, for example.

The present surgical laser technology, particularly for carbon dioxide lasers, requires cavity folding when power in excess of 60 or 70 watts is required. This is true of both flowing gas and sealed lasers.

With the technique known as cavity folding, two gain sections are connected in a series arrangement. The laser beam from the first gain section is folded into a second gain section with a total output beam power from the second gain section of approximately the combined power of both individual sections. The problem with this technique is that the two gain sections and accessory optical components, such as mirrors for folding the laser beams, must be very accurately aligned. If the laser beam from the first gain section is misaligned as it impinges on the second gain section, the individual sections may stop lasing altogether and no output will result.

Without the use of folding, if a single laser is used, the laser cavity will become impossibly long to package in an ergonomic manner.

Experience teaches that folded lasers never remain as well aligned as single pass lasers since there are between one and two additional mirrors and mounts in the resonant cavity as well as beam tubes, all of which must be mechanically very stable with respect to a common reference, the frame of the laser. The more mirror mounts and frame members, i.e., tubes, supports and braces, the more accumulated angular mirror motion that results due to temperature changes, relief of stresses over time and movement. This seriously impairs cavity resonance and reduces output power and mode quality.

Applicant is aware of the following references which relate to the laser art:
4,649,351- Veldkamp et al 4,220,928- Bloom et al
4,550,240- Toida et al 4,364,014- Gray
4,573,465- Sugiyama et al 3,950,707- Hill et al
4,672,969- Dew 4,396,284- Presta, et al U.S. Pat. No. 4,649,351 to Veldkamp et al describes an apparatus and method for coherently adding laser beams. The patent discloses an apparatus provided for summing a plurality of lasers coherently by phase locking the plurality of lasers and by diffracting a plurality of beams into a single beam. A defraction grating is utilized having a configuration to generate upon illumination substantially equal intensities of diffraction orders corresponding to the number of lasers while suppressing higher unwanted orders. Phase locking is accomplished by a single master laser, or by a cavity mirror to generate reference beams. The output beams of the plurality of lasers are coherently superimposed by the grating.

U.S. Pat. No. 4,550,240 to Toida et al discloses a laser irradiating apparatus comprising a first laser source for outputting a first laser beam and a second laser source for outputting a second laser beam. The laser beams are selectively irradiated through either a first light guide or a second light guide. A first laser beam and a second laser beam are combined by mixing means comprising a plurality of mirrors and a dichroic mirror which transmits the light from the first laser beam and reflects the light from the second laser beam.

U.S. Pat. No. 4,573,465 to Sugiyama et al shows an apparatus where two laser sources are combined using a dichroic mirror, similar to the Toida et al reference. The laser irradiation apparatus of the Sugiyama et al patent irradiates a plurality of working laser beams having different wavelengths to obtain complex effects in medical treatment.

U.S. Pat. No. 4,672,969 to Dew discloses a laser healing method in which the laser beams from a first laser and an auxiliary laser are provided to an area of medical treatment by optical elements.

U.S. Pat. No. 4,396,285 to Presta et al discloses a laser system for medical applications having two lasers and a movable concave reflector. The lasers are capable of generating beams of coherent electromagnetic radiation. One of the beams, an aiming beam, is aligned to impinge the reflector, to reflect therefrom and to impinge a biological specimen. The reflector is moved until the beam is aligned to impinge the desired position. The reflector is held stationary and the second beam is generated. The second beam is also aligned to impinge the reflector to reflect therefrom and to impinge the same desired position as that impinged by the first beam. This reference shows a conventional type of structure in which the first beam is used for aiming or guiding purposes and the second laser beam is utilized for the actual treatment.

SUMMARY OF THE INVENTION

It is an object of the present invention to provide a laser system in which the laser beams from at least two individual lasers are combined to provide an output beam of approximately the sum of the powers of the individual lasers.

It is furthermore an object of the invention to provide such a laser beam combining the laser beams of at least two individual lasers which avoids the problems encountered in cavity folding type systems.

It is yet a further object of the present invention to provide such a laser system which is particularly useful in surgical laser systems.

It is yet still a further object of the present invention to provide such a laser system which is relatively insensitive to movement, temperature changes, stresses, relief small variations of polarization rotation of individual laser beams and small changes in optical element positions.

In particular, it is an object of the present invention to provide a laser system wherein the laser beams of two individual lasers are combined, resulting in a laser beam of approximately double the power of each of the two individual lasers.

It is yet still a further object to provide such a laser system wherein the combined beam is generated by appropriately polarizing the two individual beams and providing the individual beams to a polarization selective device such as a thin film polarizer, resulting in a common colinear output beam.

The above and other objects of the present invention are achieved by an apparatus for combining two laser beams each having a power level into a common colinear laser beam having a power level that is the sum of the power levels of the two laser beams, comprising a support, means disposed on the support having a first surface upon which a first of the laser beams impinges for transmitting the first laser beam with substantially full power transmission along an axis and having a second surface upon which the second laser beam impinges for reflecting the second laser beam with substantially full power along the axis, resulting in a common colinear beam along the axis, and means disposed on the support for providing the first and second laser beams to the means for transmitting and reflecting, the first and second laser beams being substantially orthogonally polarized with respect to each other.

The invention utilizes two independent lasers operating in parallel, with the polarization of each laser being made orthogonal to the other. Thus, the electric field vector of the first laser beam will be perpendicular to the electric field vector of the second laser beam. The beam from the first laser is transmitted to a polarization selective device, e.g., a thin film polarizer disposed at Brewster's angle. The laser beam transmitted through such a polarizer at Brewster's angle will be transmitted with approximately 100% power, i.e., there will be substantially no loss.

The beam from the second laser, polarized at 90° with respect to the beam from the first laser, is reflected by a simple mirror at an angle to the polarization selective device. If a thin film polarizer is used, it is coated with a coating which is reflective to a laser beam having a polarization orthogonal to the first laser beam, and which transmits the first laser beam substantially without loss. Typically, approximately 95% of the power from the second orthogonally polarized laser beam will be reflected by the thin film polarizer, thus resulting in a combined laser beam which has the power of approximately the sum of the two individual lasers.

The advantage of the invention is that alignment of the two lasers is not critical. Each laser can operate independently and is not dependent upon accurate alignment of the laser beam from the other laser in order to continue to lase. Even if the beams are slightly misaligned, the only result is that the combined laser beam appears slightly elliptical instead of circular, but especially for medical treatment purposes, this slight elliptical characteristic is unimportant.

Other objects, features and advantages of the present invention will be apparent from the detailed description which follows.

BRIEF DESCRIPTION OF THE DRAWING

The invention will be described in greater detail in the following detailed description with reference to the single drawing FIGURE which shows an embodiment of apparatus according to the present invention for providing an output laser beam which is approximately the sum of the powers of two individual laser beams.

DETAILED DESCRIPTION

With reference now to the drawing FIGURE, the invention provides that two independent lasers A and B be mounted on a rigid base plate K upon which is disposed a mixer box G. The beams A' and B' of each laser A and B are highly polarized by any of several methods known to the art. The polarization of laser A may be horizontal, for example, i.e., in the plane of the FIGURE. The polarization of laser B is made orthogonal with respect to that of laser A, and in the embodiment shown, is vertical, or directed normal to the plane of the FIGURE. Another wa to describe the polarization of each laser is to say that with reference to optical element E, in the illustrated embodiment, a thin film polarizer, or Brewster plate, to be described later, beam A' is "P-pol" and beam B' is "S-pol", which are terms readily known to the art. A further optical element H is disposed in line with the output of laser B, and comprises a substantially 100% reflecting mirror. The optical element H is mounted on a mount D. The beam from laser B reflected from optical element H is caused to impinge on the optical element E at the same place where the beam from laser A exits, after refraction, from optical element E. It is the nature of a Brewster plate, optical element E, to transmit, without loss, a beam that impinges with "P-pol" polarization. To achieve this, the Brewster plate must be at Brewster's angle, which is the arc tangent of the windows index of refraction n, i.e., Brewster's angle equals $\text{Tan}^{-1}n$.

If the optical element E has an index n of 2.4, for example, Brewster's angle BA is 67.4° to the optical normal, as shown.

State of the art coating technology can enhance the characteristic of a Brewster plate by coating one surface. After this coating is applied, the optical element E is known as a thin film polarizer. The coating is applied to the surface of the Brewster plate upon which the beam from laser B reflected off optical element H impinges.

The coating on the Brewster plate allows the "S-pol" of the beam from laser B to reflect with little loss, while allowing the "P-pol" of the beam from laser A to be transmitted. Without the coating of the Brewster plate, the reflection would be at best 66.3%, the combined reflection from both the front and back surfaces of optical element E. Thus, the thin film coating of optical element E enhances the "S-pol" reflection of the beam from laser B and avoids the beam quality distortion that would result from a two-surface reflection. A thin film polarizer which may be employed in the invention is available from II-VI, Inc. of Saxonburg, PA, part #TFP-Z-0.60-M.

The resulting beam F, which is a combination of the beam from laser A refracted through the Brewster plate and the reflected beam from laser B, comprises the two beams travelling coaxially together, but independently, i.e., the two beams combined as beam F do not constructively or destructively interfere with each other.

In addition to the use of a thin film polarizer as element E, other polarization selective optics known to those of skill in the art may also be used, for example, wire grid polarizers. If a wire grid polarizer is used, it may be disposed at angles other than Brewster's angle.

This dual beam combination technique allows two stable unfolded (single pass) lasers to combine outputs into one beam even if there is a slight misalignment of each beam which would be perceived as a slightly elongated spot at the target. However, this slightly elongated or elliptical characteristic of the spot is not a particular problem, especially for surgical laser applications.

The angular misalignment between lasers A, B and mixer G that can be tolerated is 50 to 100 times greater than that of equivalent structures in a folded laser of equivalent output power.

The invention also provides a means to achieve the beam combination through the use of two special purpose mounts I and D that incorporate the required degrees of freedom to achieve alignment without redundant motions. Mount I for the thin film polarizer E rotates about the axis of the beam from laser A. Mount D pivots mirror H with a limited motion (arrow R) in the horizontal plane of the drawing FIGURE about the surface of the mirror about axis N, which is normal to the plane of the paper and disposed at the point of impingement of the beam from laser B on the mirror. Mirror H can also be moved in and out of mount D, i.e., horizontally, as shown by arrows P and rotated about the longitudinal axis of mount D to achieve position adjustments of the beam from laser B on optical element E, as shown by arrow Q.

The three degrees of freedom of mount D combined with the single rotational degree of freedom in mount I allow colinear alignment of the beam from laser B to the fixed beam from laser A. Thus, translation of mirror H along the longitudinal axis of mount D (T) and the pivoting about axis N allows adjustment of the point of impingement of the beam from laser B on optical element E in the plane of the paper. Rotation about the longitudinal axis T as shown by arrows Q and the rotation of mount I for the optical element E about the axis of the beam from laser A allows for adjustment in the plane normal to the plane of the paper. This allows for proper registration of the beams from the two lasers A and B.

It may also be possible to eliminate mirror H by directly aiming laser B so that its output beam impinges directly on optical element E at the point where the beam from laser A emerges from optical element E. A suitable mechanical mount for aligning laser B would then be required.

Additionally, a shutter blade C can be positioned at a complementary Brewster's angle CA with respect to beam A, i.e., at 90° minus 67.4° equals 22.6°, in the embodiment shown, cutting across both the beams from lasers A and B before they reach the optical element E. If the blade C is reflective, it will direct the two beams to a common point between the lasers where a power measuring sensor L and beam dump can be conveniently placed. The shutter C can be translated by a shutter solenoid so that the shutter will intercept both the beams from lasers A and B. In the position shown, the shutter intercepts neither beam, as the shutter is disposed such that it does not cut across the path of the beams from laser A and an aperture is placed in the shutter at an appropriate spot such that the beam from laser B is transmitted to the optical element E. Alternatively, the shutter can be constructed so that it has two apertures along its length such that both beams are transmitted to the optical element E when it is desired not to intercept the beams.

A similar shutter can be incorporated to move a partially reflective optical element into and out of one beam to achieve greater dynamic range of powers if current control of the laser power does not provide enough range. Other mounts and optical elements can be mounted in the mixing box G to mix other laser beams with the beams from lasers A and B, using, for example, an optical element J, which may comprise a standard dual wavelength beam combiner. As shown, a conventional visible wavelength guide beam (e.g., HeNe) is combined with the output beam using optical element J after it is reflected from a mirror M. Optical element J may be disposed on a mount similar to mount I and optical element M may be mounted on a mount U similar to mount D.

The mixer box J and the optics mounted thereon are securely attached to the baseplate K to which the lasers A and B are mounted, thus providing a common reference to maintain angular alignment of all components.

In the foregoing specification, the invention has been described with reference to a specific exemplary embodiment thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. Apparatus for combining two laser beams each having a power level into a common colinear laser beam having a power level that is the sum of the power levels of the two laser beams comprising:
   a support;
   means disposed on the support having a first surface upon which a first of the laser beams impinges for transmitting the first laser beam with substantially full power transmission along an axis and having a second surface upon which the second laser beam impinges for reflecting the second laser beam with substantially full power along the axis, resulting in a common colinear beam along said axis, said means for transmitting and reflecting comprising a thin film polarizer disposed at Brewster's angle with respect to a normal to the axis of the first of said laser beams; and
   means disposed on the support for providing said first and second laser beams to said means for transmitting and reflecting;
   said first and second laser beams being substantially orthogonally polarized with respect to each other and being of the same wavelength.

2. The apparatus recited in claim 1, wherein the second surface of the thin film polarizer comprises a coated surface.

3. The apparatus recited in claim 1, wherein said means for providing comprises a mirror disposed in the path of the second laser beam for reflecting the second laser beam to the second surface of said means for transmitting and receiving at a location on said second surface at which said first laser beam exits the second surface.

4. The apparatus recited in claim 3, further comprising a mount for mounting said mirror, said mount being movable to pivot said mirror about an axis disposed along a surface of the mirror and perpendicular to the axis of said second laser beam impinging said mirror.

5. The apparatus recited in claim 4, wherein said mount allows said mirror to be translated along an axis disposed orthogonally to a direction at which the second laser beam impinges on said mirror.

6. The apparatus recited in claim 5, wherein said mount allows said mirror to be rotated about the axis of the translation.

7. The apparatus recited in claim 6, further comprising a second mount, said second mount supporting said means for transmitting and reflecting, said second mount allowing rotation of said means for transmitting and reflecting about the axis of said first laser beam.

8. The apparatus recited in claim 1, further comprising power sensing and dump means, and further comprising shutter means for movement into the path of said first and second laser beams for reflecting said laser beams to said power sensing and dump means.

9. The apparatus recited in claim 8, wherein said shutter means is translatably movable into the path of said first and second laser beams.

10. The apparatus recited in claim 1, further comprising power sensing and dump means, and further comprising shutter means for movement into the path of said first and second laser beams for reflecting said laser beams to said power sensing and dump means.

11. The apparatus recited in claim 10, wherein said shutter means is translatably movable into the path of said first and second laser beams and is disposed at an angle complementary to Brewster's angle for said first laser beam.

12. The apparatus recited in claim 1, further comprising additional optical means for combining an additional laser beam with said common colinear beam.

13. The apparatus recited in claim 12, wherein said additional laser beam comprises a visible light guide beam.

14. The apparatus recited in claim 1, wherein said common colinear beam is provided for medical treatment.

15. A method for combing two laser beams each having a power level into a common colinear laser beam having a power level that is the sum of the power levels of the two laser beams comprising the steps of:
    substantially orthogonally polarizing said two laser beams with respect to each other, said two laser beams having the same wavelength;
    disposing a thin film polarizer at Brewster's angle with respect to a normal to an axis of the first of said laser beams; and
    transmitting the first laser beam through the polarizer with substantially full power transmission along the axis and reflecting the second laser beam from a surface of the polarizer with substantially full power along the axis, resulting in a common colinear beam along said axis.

16. The method recited in claim 15, further comprising disposing a mirror in the path of the second laser beam for reflecting the second laser beam to the surface of the polarizer at a location on said surface at which said first laser beam exits the surface.

17. The method recited in claim 16, further comprising movably mounting said mirror for pivotal motion about an axis disposed along a surface of the mirror and perpendicular to the axis of said second laser beam impinging said mirror.

18. The method recited in claim 17, further comprising translating said mirror along a axis disposed orthogonally to a direction at which the second laser beam impinges on said mirror.

19. The method recited in claim 18, further comprising rotating said mirror about the axis of the translation.

20. The method recited in claim 19, further comprising rotating said polarizer about the axis of said first laser beam.

21. The method recited in claim 15, further comprising intercepting the path of said first and second laser beams and reflecting said laser beams to a location for at least one of power measurement and energy absorption.

22. The method recited in claim 15, further comprising intercepting the path of said first and second laser beams and reflecting said laser beams to a location for at least one of power measurement and energy absorption.

23. The method recited in claim 22, wherein said step of intercepting comprises translating a shutter disposed at an angle complementary to Brewster's angle for said first laser beam into the path of said first and second laser beams.

24. The method recited in claim 15, further comprising combining an additional laser beam with said common colinear beam.

25. The method recited in claim 24, wherein said additional laser beam comprises a visible light guide beam.

26. The method recited in claim 15, further comprising providing said common colinear beam to an area of medical treatment.

* * * * *